United States Patent
De La Poterie et al.

(10) Patent No.: US 6,682,748 B1
(45) Date of Patent: Jan. 27, 2004

(54) TRANSFER-FREE COSMETIC COMPOSITION COMPRISING A DISPERSION OF POLYMER PARTICLES IN A LIQUID FATTY PHASE AND A FAT-SOLUBLE POLYMER

(75) Inventors: Valérie De La Poterie, Le Chatelet en Brie (FR); Nathalie Mougin, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/218,459

(22) Filed: Dec. 22, 1998

(30) Foreign Application Priority Data

Dec. 22, 1997 (FR) .............................. 97 16254

(51) Int. Cl.$^7$ ........................ A61K 6/00; A61K 7/021; A61K 7/025; A61K 31/74
(52) U.S. Cl. ........................ 424/401; 424/63; 424/64; 424/69; 424/78.02; 514/937
(58) Field of Search ................. 424/400, 401, 424/63, 64, 69; 514/78.02, 78.03, 844, 937

(56) References Cited

U.S. PATENT DOCUMENTS

| | | | |
|---|---|---|---|
| 5,356,627 A | | 10/1994 | Da Cunha et al. |
| 5,725,845 A | * | 3/1998 | Krog et al. .................... 424/64 |
| 5,945,095 A | * | 8/1999 | Mougin et al. .......... 424/78.02 |
| 6,254,876 B1 | * | 7/2001 | de la Poterie |

FOREIGN PATENT DOCUMENTS

EP     0 749 746 A1     12/1996

WO     97/00662     1/1997

OTHER PUBLICATIONS

"Make-Up Mania/Girl Talk"; www.thefrugalface.com/girl-talk; pp1-5.
Patent Abstract of Japan vol. 017, No. 291, (C-1067), Jun. 4, 1993 & JP 05 017338 A (Kao Corp), Jan. 26, 1993.

* cited by examiner

Primary Examiner—Michael G. Hartley
Assistant Examiner—Sharmila S. Gollamudi
(74) Attorney, Agent, or Firm—Oblon, Spivak, McClelland, Maier & Neustadt, P.C.

(57) ABSTRACT

A composition suitable for topical application, which contains:
- a liquid fatty phase,
- at least one coloring agent,
- at least 2% by weight, with respect to the total weight of the composition, of a polymer which is dispersible in the liquid fatty phase, and
- a polymer which is soluble in the liquid fatty phase.

In preferred embodiments, the composition may be provided in the form of a cast product or of a gel containing at least one coloring material, in particular pulverulent coloring material, a dispersion of polymer particles which are stabilized at the surface in a liquid fatty phase and a fat-soluble polymer of the vinylpyrrolidone copolymer type. In addition, according to the amount of polymer, it is possible to obtain, on the lips or skin, a supple film having notable transfer-free properties while being extremely comfortable. The invention also relates to the use of this dispersion in such a composition.

109 Claims, No Drawings

TRANSFER-FREE COSMETIC COMPOSITION COMPRISING A DISPERSION OF POLYMER PARTICLES IN A LIQUID FATTY PHASE AND A FAT-SOLUBLE POLYMER

BACKGROUND OF THE INVENTION

1. Field of the Invention

The present invention relates to a composition comprising a polymer which is dispersible in a fatty phase and a fat-soluble polymer, which may be used in particular, for the cosmetic, dermatological, pharmaceutical and hygiene fields. More particularly, the invention relates to a transfer-free composition for caring for and/or making up the skin, both of the human face and of the human body, mucous membranes, such as the lips and the interior of the lower eyelids, or superficial body growth, such as the eyelashes, eyebrows, nails and hair.

The inventive composition can be provided in particular in the form of a product cast as a stick or as a dish, such as lipsticks or lip balms, cast foundations, products for concealing rings under the eyes, eyeshadows or blushers, or in the form of a more or less fluid paste or cream, such as fluid foundations or lipsticks, eyeliners, solar protection compositions or compositions for coloring the skin.

2. Background of the Invention

The products for making up or caring for the skin or lips of human beings, such as foundations or lipsticks, generally comprise fatty phases, such as waxes and oils, pigments and/or fillers and, optionally, additives, such as cosmetic or dermatological active principles. They can also comprise so-called "pasty" products with a supple consistency which make it possible to produce colored or non-colored pastes to be applied with a brush.

These compositions, when they are applied to the skin or the lips, exhibit the disadvantage of transferring, that is to say of being at least partly deposited and leaving traces on certain substrates with which they can be brought into contact, in particular a glass, a cup, a cigarette, an item of clothing or the skin. This results in mediocre persistence of the applied film, requiring the regular renewal of the application of the foundation or lipstick composition. Furthermore, the appearance of these unacceptable traces, in particular on blouse collars, can dissuade some women from using this type of make-up.

For some years, cosmetic scientists have been interested in lipstick compositions and more recently in foundation compositions which are "transfer-free". Thus, Shiseido described in JP-A-61-65809, "transfer-free" lipstick compositions comprising a siloxysilicate resin (with a three-dimensional network), a volatile silicone oil with a cyclic silicone chain and pulverulent fillers. Likewise, Noevier described in JP-A-62-61911, "transfer-free" lipstick, eyeliner and foundation compositions comprising one or more volatile silicones in combination with one or more hydrocarbon-comprising waxes.

These compositions, although exhibiting improved "transfer-free" properties, have the disadvantage of leaving on the lips, after evaporation of the silicone oils, a film which becomes uncomfortable over time (feeling of drying and of tautness), dissuading a number of women from this type of lipstick. In order to improve the comfort of this type of composition, non-volatile silicone or non-silicone oils could be added but, in this case, "transfer-free" efficiency is lost.

More recently, Procter & Gamble has described in WO-A-96/36308, mascara compositions of water-in-oil emulsion type which exhibit a lengthy hold and resistance to water and which do not leave traces. These compositions comprise, inter alia, a water-insoluble polymer, generally known as a latex, in combination with a lipophilic polymer of the copolymer type, a surfactant of the alkyl or alkoxy dimethicone copolyol type, hydrocarbon-comprising oils, pigments and fillers, as well as waxes.

Compositions based on silicone oils and silicone resins, as well as those based on latex, result in matt colored films. Now, women today are looking for products, in particular for coloring the lips, which are glossy. Furthermore, the transfer-free properties of the films deposited are not perfect. In particular, pronounced pressure or rubbing results in a decrease in the color of the deposit and in a redeposition on the substrate brought into contact with these films.

In addition, EP-A-497,144 and FR-A-2,357,244 describe so-called "transfer-free" compositions comprising a styrene-ethylene-propylene block polymer in combination with waxes, light or volatile oils, and pigments. These compositions exhibit the disadvantage of being not very comfortable, of having indifferent cosmetic properties and of being difficult to formulate. Furthermore, the "transfer-free" properties of these compositions are very mediocre, at best.

The need thus remains for a composition which does not exhibit the above disadvantages and which has in particular total "transfer-free" properties, even during pronounced or intensive pressure or rubbing, and a more or less glossy appearance, suited to the wish of the consumer, and which does not dry over time the skin or the lips on which it is applied.

SUMMARY OF THE INVENTION

The inventors have found, entirely surprisingly, that the use of a polymer which is dispersible in a fatty phase and of a fat-soluble polymer in a cosmetic, dermatological, pharmaceutical or hygiene composition provides a glossy film, with very good hold, which does not transfer at all and which is resistant to water, while being very pleasant on application and to wear throughout the day. The film is in particular supple, flexible, non-greasy and non-sticky.

Thus, the present invention includes a composition for topical application comprising a liquid fatty phase, characterized in that it additionally comprises at least 2% by weight, with respect to the total weight of the composition, of polymer which is dispersible in the liquid fatty phase and a polymer which is soluble in the fatty phase.

This composition is in particular a cosmetic, dermatological, hygiene or pharmaceutical composition. It thus comprises ingredients which are compatible with the skin, mucous membranes and keratinous fibers or superficial body growth.

Another subject of the invention is a composition which is provided in the form of a cast product and which comprises at least one cosmetic, dermatological, hygiene or pharmaceutical liquid fatty phase and at least one wax which is solid at room temperature, characterized in that it additionally comprises at least 2% by weight, with respect to the total weight of the composition, of polymer which is dispersible in the liquid fatty phase and at least one polymer which is soluble in the fatty phase.

The composition advantageously comprises ingredients chosen from cosmetic, dermatological, hygiene or pharmaceutical active principles and coloring materials.

The dispersible polymer or polymers which can be used in the present application can be of any nature. Thus, it is possible to employ a radical polymer, a polycondensate, even a polymer of natural origin, and their mixtures. The polymer can be chosen by the person skilled in the art as a function of its properties and according to the subsequent application desired for the composition. Thus, the polymer may or may not be able to form a film.

However, the production of an entirely "transfer-free" film is more especially due to the use of a polymer which can form a film.

The composition of the invention may comprise one or more polymers which are soluble in the liquid fatty phase exhibiting a mean molecular weight of 500 to 1,000,000 and better still of 5,000 to 15,000. Such fat-soluble polymers play in particular the role of plasticizer of the film, enhancing its hold over time, a property independent of the transfer-free properties, without, however, rendering it sticky. These polymers may or may not be gelling agents of the liquid fatty phase. They make it possible to increase the viscosity of the composition as well as the satiny, indeed glossy, appearance of the film. Thus, by varying the amount of these polymers and their nature, it is possible to adjust the gloss of the film, which is much valued by formulators and users.

The fat-soluble polymers of the composition of the invention are preferably used in an amount of 0.5% to 40% (as active material) of the total weight of the composition and preferably of 2% to 20%. These fat-soluble polymers preferably exhibit a softening temperature at most equal to 30° C.

Mention may be made, by way of example of fat-soluble polymers which can be used in the invention, of: polyalkylenes, in particular polybutene, poly(meth)acrylates, alkylcelluloses with a saturated or unsaturated, linear or branched, $C_1$ to $C_8$ alkyl radical, such as ethylcellulose and propylcellulose, silicone polymers which are compatible with the fatty phase and copolymers of vinylpyrrolidone (VP), and their mixtures.

Use is preferably made of copolymers of vinylpyrrolidone and of $C_2$ to $C_{40}$ alkene and better still $C_3$ to $C_{20}$ alkene. Mention may be made, by way of example of VP copolymer which can be used in the invention, of the VP/vinyl acetate, VP/ethyl methacrylate, VP/ethyl methacrylate/methacrylic acid, VP/eicosene, VP/hexadecene, VP/triacontene, VP/styrene or VP/acrylic acid/lauryl methacrylate copolymer or butylated polyvinylpyrrolidone (PVP).

Use is preferably made, not only for the properties of gloss but also of feel and of consistency of the film, of the PVP/hexadecene copolymer having an average molecular weight of 7000 to 7500 or of the PVP/ eicosene copolymer having an average molecular weight of 8000 to 9000.

Another subject of the invention is a composition comprising a cosmetic, dermatological, hygiene or pharmaceutical volatile liquid fatty phase, at least 2% by weight, with respect to the total weight of the composition, of polymer which is dispersible in the fatty phase, at least one polymer which is soluble in the fatty phase and at least one ingredient chosen from cosmetic, dermatological, hygiene or pharmaceutical active principles and optionally coloring materials.

Another subject-matter of the invention is the use, in or for the manufacture of a composition in the form of a cast product comprising at least one cosmetic, dermatological, hygiene or pharmaceutical liquid fatty phase and at least one wax, in particular a wax which is solid at room temperature, of at least one polymer which is dispersible in the liquid fatty phase and of a polymer which is soluble in this fatty phase, in order to decrease, indeed eliminate, the transfer of the composition film deposited on the mucous membranes, such as the lips, and/or on the skin.

Another subject of the invention is the use, in a cosmetic, dermatological, pharmaceutical or hygiene composition or for the manufacture of a cosmetic, dermatological, pharmaceutical or hygiene composition, of at least one polymer, which can form a film, which is dispersible in a liquid fatty phase and of a polymer which is soluble in the fatty phase, in order to decrease, indeed eliminate, the transfer of the composition film deposited on the mucous membranes and/or the skin of human beings to a substrate brought into contact with the film.

Another subject of the invention is the use, in or for the manufacture of a composition for topical application comprising a liquid fatty phase and at least one ingredient chosen from cosmetic, dermatological, hygiene and pharmaceutical active principles, coloring materials and their mixtures, of at least one polymer which is dispersible in the liquid fatty phase and of at least one polymer which is soluble in this fatty phase, in order to decrease, indeed eliminate, the transfer of the composition film deposited on the skin and/or the mucous membranes, such as the lips.

An additional subject of the invention is a process for the cosmetic care of or for making up the lips or the skin, which consists in applying, to the lips or the skin respectively, a cosmetic composition as defined above.

A further subject of the invention is a process for limiting, indeed eliminating, the transfer of a composition for making up or caring for the skin or lips onto a substrate other than the skin and the lips, comprising a liquid fatty phase and at least one ingredient chosen from coloring materials and cosmetic, dermatological, hygiene and pharmaceutical active principles and their mixtures, which consists in introducing, into the liquid fatty phase, at least one polymer which is dispersible in the liquid fatty phase and at least one polymer which is soluble in this fatty phase.

A more complete appreciation of the invention and many of the attendant advantages thereof will be readily obtained as the same becomes better understood by reference to the following detailed description.

DETAILED DESCRIPTION OF THE INVENTION

The dispersible polymer is advantageously provided in the form of dispersed particles which are stabilized at the surface by at least one stabilizing agent. It represents at least 2% of the total weight of the composition.

One advantage of the use of a dispersion of particles in a composition of the invention is that the particles remain in the state of individual particles, without forming agglomerates, in the fatty phase, which would not be the case with inorganic particles of nanometric size. Another advantage of the polymer dispersion is the possibility of obtaining very fluid compositions (of the order of 130 centipoises), even in the presence of a high level of polymer.

Yet another advantage of such a dispersion is that it is possible to grade, as desired, the size of the polymer particles and to adjust their "polydispersity" in size during the synthesis. It is thus possible to obtain particles of very small size, which are invisible to the naked eye when they are in the composition and when they are applied to the skin or lips. This would be impossible with pigments in particulate form, their composition not allowing the mean size of the particles to be varied.

In addition, it has been found that the compositions according to the invention exhibit particularly advantageous qualities of spreading over and of adhesion to the skin, semi-mucous membranes or mucous membranes, as well as a smooth and pleasant touch. These compositions have, in addition, the advantage of being easy to take off, in particular with a conventional make-up removal milk. This is entirely remarkable, since the compositions of the prior art with high "transfer-free" properties are very difficult to remove. In general, they are sold with a specific make-up removal product, which introduces an additional restriction for the user.

The compositions according to the invention thus advantageously comprise a stable dispersion of generally spherical particles of at least one polymer in a physiologically acceptable liquid fatty phase. These dispersions can in particular be provided in the form of nanoparticles of polymers as a stable dispersion in the fatty phase. The nanoparticles preferably have a size of between 5 and 600 nm, given that, beyond approximately 600 nm, the dispersions of particles become much less stable. This size range includes all specific values and subranges therebetween, including 10, 25, 50, 100, 200, 300, 400 and 500 nm.

A further advantage of the polymer dispersion of the composition of the invention is the possibility of varying the glass transition temperature (Tg) of the polymer or of the polymeric system (polymer plus additive of the plasticizer type) and of thus changing from a soft polymer to a more or less hard polymer, making it possible to adjust the mechanical properties of the compositions as a function of the envisaged application.

It is possible to use dispersible polymers, which can form films, preferably having a low Tg of less than or equal to the temperature of the skin. A dispersion is thus obtained which can form a film when it is applied to a substrate, which is not the case when use is made of dispersions of inorganic pigments according to the prior art.

The dispersible polymers which can be used in the composition of the invention preferably have a molecular weight (weight-average) on the order of 2000 to 10,000,000 and a Tg of −100° C. to 300° C.

.This molecular weight range includes all specific values and subranges therebetween, including 5,000, 10,000, 25,000, 50,000, 100,000, 250,000, 300,000, 500,000, 750,000 1,000,000, 2,000,000, 5,000,000 and 8,000,000. This Tg range includes all specific values and subranges therebetween, including −75, −50, −25, −10, −5, 0, 5, 10, 25, 50, 75, 100, 150, 200 and 250° C.

When the dispersible polymer exhibits a glass transition temperature which is too high for the desired application, it is possible to combine it with an additional plasticizer, other than fat-soluble polymers, so as to lower this temperature of the mixture used. The additional plasticizer can be chosen from plasticizers normally used in the field of application and in particular from compounds which can be solvents of the polymer.

Mention may be made, among dispersible polymers which can form films, of acrylic or vinyl radical homopolymers or copolymers, preferably having a Tg of less than or equal to 40° C., and in particular of methyl acrylates optionally copolymerized with acrylic acid.

Mention may be made, among dispersible polymers which cannot form films, of optionally crosslinked, vinyl or acrylic, radical homopolymers or copolymers preferably having a Tg of greater than or equal to 40° C., such as poly(methyl methacrylate), polystyrene or poly(tert-butyl acrylate).

The dispersible polymers of the invention can be chosen, without implied limitation, from the following polymers or copolymers: polyurethanes, polyurethane-acrylics, polyureas, polyurea-polyurethanes, polyester-polyurethanes, polyether-polyurethanes, polyesters, polyesteramides, polyesters with a fatty chain or alkyds; acrylic and/or vinyl polymers or copolymers; acrylic-silicone copolymers; polyacrylamides, silicone polymers, fluorinated polymers and their mixtures.

The liquid fatty phase in which the polymer is dispersed can be composed of any cosmetically or dermatologically acceptable oil and more generally physiologically acceptable oil chosen in particular from carbon-comprising, hydrocarbon-comprising, fluorinated and/or silicone oils of mineral, animal, plant or synthetic origin, alone or as a mixture insofar as they form a homogeneous and stable mixture and insofar as they are compatible with the use envisaged.

"Liquid fatty phase" refers to any non-aqueous medium which is liquid at room temperature. "Volatile fatty phase" refers to mean any non-aqueous medium which is capable of evaporating from the skin or lips at room temperature in less than one hour.

Mention may thus be made of hydrocarbon-comprising oils, such as liquid paraffin or liquid petrolatum, mink oil, turtle oil, soybean oil, perhydrosqualene, sweet almond oil, calophyllum oil, palm oil, grape seed oil, sesame oil, maize oil, parleam oil, arara oil, rapeseed oil, sunflower oil, cottonseed oil, apricot oil, castor oil, avocado oil, jojoba oil, olive oil or cereal germ oil; esters of lanolic acid, of oleic acid, of lauric acid or of stearic acid; fatty esters, such as isopropyl myristate, isopropyl palmitate, butyl stearate, hexyl laurate, diisopropyl adipate, isononyl isononate, 2-ethylhexyl palmitate, 2-hexyldecyl laurate, 2-octyldecyl palmitate, 2-octyldodecyl myristate or lactate, di(2-ethylhexyl) succinate, diisostearyl malate, glyceryl triisostearate or diglyceryl triisostearate; higher fatty acids, such as myristic acid, palmitic acid, stearic acid, behenic acid, oleic acid, linoleic acid, linolenic acid or isostearic acid; higher fatty alcohols, such as cetanol, stearyl alcohol or oleyl alcohol, linoleyl or linolenyl alcohol, isostearyl alcohol or octyldodecanol; silicone oils, such as polydimethylsiloxanes (PDMS), which are optionally phenylated, such as phenyltrimethicones, or which are optionally substituted by optionally fluorinated aliphatic and/or aromatic groups or by functional groups, such as hydroxyl, thiol and/or amine groups; polysiloxanes modified by fatty acids, fatty alcohols or polyoxyalkylenes, fluorinated silicones or perfluorinated oils.

Use may advantageously be made of one or more oils which are volatile at room temperature and atmospheric pressure. These volatile oils have for example a steam pressure at room temperature >0 and in particular from $10^{-3}$ to 300 mm Hg, provided that the boiling point is >30° C. These volatile oils are favorable to the production of a film with total "transfer-free" properties. After the evaporation of these oils, a supple and non-sticky film-forming deposit is obtained on the skin or mucous membranes which respectively follows the movements of the skin or lips on which the composition is applied. In addition, these volatile oils facilitate the application of the composition to the skin, mucous membranes or superficial body growths.

These oils can be hydrocarbon-comprising oils or silicone oils optionally comprising alkyl or alkoxy groups at the end of the silicone chain or in the pendent position.

Mention may be made, as volatile oil which can be used in the invention, of linear or cyclic silicones having a viscosity less than 8 cst and having from 2 to 7 silicon atoms, these silicones optionally comprising alkyl or alkoxy groups having from 1 to 10 carbon atoms, and $C_8$–$C_{16}$ isoparaffins. These volatile oils represent in particular from 30 to 97.5% of the total weight of the composition and better still from 30 to 75%. These ranges includes all specific values and subranges therebetween, including 35, 40, 45, 50, 55, 60, 65, 70, 80, 85, 90 and 95% by weight.

Mention may be made, as volatile oil which can be used in the invention, of in particular octamethylcyclotetrasiloxane, decamethylcyclopentasiloxane, hexadecamethylcyclohexasiloxane, heptamethylhexyltrisiloxane, heptamethyloctyltrisiloxane or $C_8$–$C_{16}$ isoparaffins, such as "Isopars", Permetyls and in particular isododecane.

In a specific embodiment of the invention, the liquid fatty phase is chosen from the group comprising:

non-aqueous liquid compounds having an overall solubility parameter according to the Hansen solubility space of less than 17 $(MPa)^{1/2}$, or monoalcohols having an overall solubility parameter according to the Hansen solubility space of less than or equal to 20 $(MPa)^{1/2}$, or mixtures thereof.

The overall solubility parameter δ according to the Hansen solubility space is defined in the article "Solubility parameter values" by Eric A. Grulke in "Polymer Handbook", 3rd edition, Chapter VII, pages 519–559, incorporated herein by reference, by the relationship:

$$\delta=(d_D^2+d_P^2+d_H^2)^{1/2}$$

in which $d_D$ characterizes the London dispersion forces resulting from the formation of dipoles induced during molecular impacts, $d_P$ characterizes the forces of Debye interactions between permanent dipoles, $d_H$ characterizes the forces of specific interactions (hydrogen bond, acid/base or donor/acceptor type and the like). The definition of the solvents in the three-dimensional solubility space according to Hansen is described in the article by C. M. Hansen: "The three-dimensional solubility parameters", J. Paint Technol., 39, 105 (1967), incorporated herein by reference.

Mention may be made, among liquid fatty phases having an overall solubility parameter according to the Hansen solubility space of less than or equal to 17 $(MPa)^{1/2}$, of vegetable oils formed by esters of fatty acids and polyols, in particular triglycerides, such as sunflower oil, sesame oil or rapeseed oil, or esters derived from long-chain acids or alcohols (that is to say, having from 6 to 20 carbon atoms), in particular esters of formula RCOOR' in which R represents the residue of a higher fatty acid comprising from 7 to 19 carbon atoms and R' represents a hydrocarbon-comprising chain comprising from 3 to 20 carbon atoms, such as palmitates, adipates and benzoates, in particular diisopropyl adipate. Mention may also be made of hydrocarbons and in particular of liquid paraffin, liquid petrolatum or hydrogenated polyisobutylene, isododecane, or alternatively "Isopars", volatile isoparaffins. Mention may further be made of silicone oils, such as polydimethylsiloxanes and polymethylphenylsiloxanes, optionally substituted by optionally fluorinated aliphatic and/or aromatic groups or by functional groups, such as hydroxyl, thiol and/or amine groups, and volatile silione oils, in particular cyclic oils. Mention may also be made of solvents, alone or as a mixture, chosen from (i) linear, branched or cyclic esters having more than 6 carbon atoms, (ii) ethers having more than 6 carbon atoms, or (iii) ketones having more than 6 carbon atoms. Monoalcohols having an overall solubility parameter according to the Hansen solubility space of less than or equal to 20 $(MPa)^{1/2}$ is understood to mean aliphatic fatty alcohols having at least 6 carbon atoms, the hydrocarbon-comprising chain not comprising a substitution group. Mention may be made, as monoalcohols according to the invention, of oleyl alcohol, decanol, dodecanol, octadecanol and linoleyl alcohol.

The choice of the non-aqueous medium is made by a person skilled in the art according to the nature of the monomers constituting the dispersible polymer and/or the nature of the stabilizing agent, as indicated below.

Furthermore, the liquid fatty phase in which the polymer is dispersed can represent from 30 to 97.5% of the total weight of the composition and preferably from 30 to 75%.

These ranges includes all specific values and subranges therebetween, including 35, 40, 45, 50, 60, 70, 80, 85, 90 and 95% by weight.

The polymer dispersion can be manufactured as disclosed in EP-A-749,747, incorporated herein by reference. The polymerization can be carried out as a dispersion, that is to say by precipitation of the polymer during formation, with protection of the particles formed with a stabilizing agent.

A mixture comprising the starting monomers and a radical initiator is thus prepared. This mixture is dissolved in a solvent known, in the continuation of the present description, as "synthesis solvent". When the fatty phase is a non-volatile oil, the polymerization can be carried out in a non-polar organic solvent (synthesis solvent), the non-volatile oil (which must be miscible with the synthesis solvent) can then be added and the synthesis solvent can be selectively distilled.

A synthesis solvent is thus chosen such that the starting monomers and the radical initiator are soluble therein and the polymer particles obtained are insoluble therein, in order for them to precipitate therefrom as they are formed. In particular, the synthesis solvent can be chosen from alkanes, such as heptane, isododecane or cyclohexane.

When the fatty phase chosen is a volatile oil, the polymerization can be carried out directly in the oil, which thus also acts as synthesis solvent. The monomers must also be soluble therein, as well as the radical initiator, and the polymer obtained must be insoluble therein.

The monomers are preferably present in the synthesis solvent, before polymerization, in a proportion of 5–20% by weight of the reaction mixture. All the monomers can be present in the solvent before the beginning of the reaction or a portion of the monomers can be added as the polymerization reaction proceeds.

The radical initiator can be in particular azobisisobutyronitrile or tert-butyl peroxy(2-ethylhexanoate).

The dispersible polymer particles are stabilized at the surface, during the polymerization, by virtue of a stabilizing agent which can be a sequential polymer, a grafted polymer and/or a random polymer, alone or as a mixture. The stabilization can be carried out by any known means and in particular by direct addition of the sequential polymer, grafted polymer and/or random polymer during the polymerization.

The stabilizing agent is preferably also present in the mixture before polymerization. However, it is also possible to add it continuously, in particular when the monomers are also added continuously.

Use can be made of 2–30% by weight of stabilizing agent with respect to the starting mixture of monomers and preferably of 5–20% by weight. These ranges includes all specific values and subranges therebetween, including 3, 4, 10, 12, 15 and 18% by weight.

When a grafted and/or sequential polymer is used as stabilizing agent, the synthesis solvent is chosen such that at least a portion of the grafts or sequences of the stabilizing polymer is soluble in the solvent, the other portion of the grafts or sequences not being soluble therein. The stabilizing polymer used during the polymerization must be soluble, or dispersible, in the synthesis solvent. Furthermore, the choice is preferably made of a stabilizing agent for which the insoluble sequences or grafts exhibit a degree of affinity for the polymer formed during the polymerization.

Mention may be made, among grafted polymers, of silicone polymers grafted with a hydrocarbon-comprising chain; hydrocarbon-comprising polymers grafted with a silicone chain; grafted copolymers having, for example, an insoluble backbone of polyacrylic type with soluble grafts of polyhydroxystearic acid type, or copolymers based on acrylates or methacrylates of $C_1$–$C_4$ alcohols and on acrylates or methacrylates of $C_8$–$C_{30}$ alcohols, such as the stearyl methacrylate/methyl methacrylate copolymer.

Mention may be made, as grafted or sequential block copolymers comprising at least one block of polyorganosiloxane type and at least one block of a radical polymer, of grafted copolymers of acrylic/ silicone type which can be employed in particular when the non-aqueous medium is a silicone medium.

Use may be made, as grafted or sequential block copolymers comprising at least one block of polyorganosiloxane type and at least one block of a polyether, of dimethicone copolyols, such as those sold under the name "Dow Corning 3225C" by Dow Corning, or lauryl methicones, such as those sold under the name "Dow Corning Q2-5200" by Dow Corning.

Mention may be made, as grafted or sequential block copolymers comprising at least one block resulting from the polymerization of monomer(s) with ethylene bond(s) eventually conjugated, generally called hydrogenated or non-hydrogenated diene(s) and at least one block of a vinyl polymer, of sequential copolymers, in particular of "diblock" or "triblock" type, of the polystyrene/ polyisoprene or polystyrene/butadiene type, such as those sold under the name of "Luvitol HSB" by BASF, of the polystyrene/copoly(ethylene-propylene) type, such as those sold under the name of "Kraton" by Shell Chemical Co., or of the polystyrene/copoly(ethylene-butylene) type.

Mention may be made, as grafted or sequential block copolymers comprising at least one block resulting from the polymerization of a hydrogenated or non-hydrogenated diene and at least one block of an acrylic polymer, of poly(methyl methacrylate)/polyisobutylene bi- or trisequential copolymers or of grafted copolymers with a poly(methyl methacrylate) backbone and with polyisobutylene grafts.

Mention may be made, as grafted or sequential block copolymers comprising at least one block resulting from the polymerization of a hydrogenated or non-hydrogenated diene and at least one block of a polyether, of polyoxyethylene/polybutadiene or polyoxyethylene/ polyisobutylene bi- or trisequential copolymers.

When a random polymer is used as stabilizing agent, it is chosen so that it has a sufficient amount of groups rendering it soluble in the envisaged synthesis solvent.

It is thus possible to employ copolymers of acrylates or methacrylates of $C_1$–$C_4$ alcohols and of acrylates or methacrylates of $C_8$–$C_{30}$ alcohols. Mention may in particular be made of the stearyl methacrylate/methyl methacrylate copolymer.

The choice is preferably made, as stabilizing agent, of a polymer which introduces the completest possible covering of the particles, several chains of stabilizing polymers then being adsorbed on one particle of polymer obtained by polymerization.

In this case, it is then preferable to use, as stabilizing agent, either a grafted polymer or a sequential polymer, so as to have a better interfacial activity. This is because the sequences or grafts which are insoluble in the synthesis solvent contribute a bulkier covering to the surface of the particles.

Furthermore, when the liquid fatty phase comprises at least one silicone oil, the stabilizing agent is preferably chosen from the group consisting of grafted or sequential block copolymers comprising at least one block of polyorganosiloxane type and at least one block of a radical polymer or of a polyether or of a polyester.

When the liquid fatty phase does not comprise a silicone oil, the stabilizing agent is preferably chosen from the group consisting of:

(a) grafted or sequential block copolymers comprising at least one block of polyorganosiloxane type and at least one block of a radical polymer or of a polyether or of a polyester, (b) copolymers of acrylates or methacrylates of $C_1$–$C_4$ alcohols and of acrylates or methacrylates of $C_8$–$C_{30}$ alcohols, (c) grafted or sequential block copolymers comprising at least one block resulting from the polymerization of a hydrogenated or non-hydrogenated diene and at least one block of a vinyl or acrylic polymer or of a polyether or of a polyester, or their mixtures.

The dispersions obtained can then be used in a composition, in particular a cosmetic, dermatological, pharmaceutical and/or hygiene composition, such as a composition for caring for or for making up the skin or lips, or alternatively a hair composition or an anti-sun composition or a composition for coloring the skin.

Depending on the application, it is possible to choose to use dispersions of polymers, which can or cannot form films, in volatile or non-volatile oils.

The composition can comprise, as coloring material, one or more pulverulent compounds and/or one or more fat-soluble colorants, for example in a proportion of 0.01 to 70% of the total weight of the composition. The pulverulent compounds can be chosen from pigments and/or pearlescent agents and/or fillers commonly used in cosmetic or dermatological compositions. The pulverulent compounds advantageously represent from 0.1 to 40% of the total weight of the composition and better still from 1 to 30%. The smaller the amount of pulverulent compounds, the better the transfer-free and comfort qualities. The fact that the transfer-free properties are enhanced as the amount of pulverulent compounds decreases is entirely surprising. This is because, until now, the transfer-free properties of the compositions of the prior art were enhanced with the amount of pulverulent compounds. Conversely, their discomfort and their dryness on the skin or mucous membranes increased.

Furthermore, the transfer-free property is enhanced with the amount of polymer which is dispersible in the liquid fatty phase. In practice, the polymer can represent, as active material, up to 60% (as active material or dry matter) of the total weight of the composition. On using more than 12% by weight, with respect to the total weight of the composition, of active polymer material in the composition and up to 60%, a total transfer-free film is obtained. Between 2 and 12%, the transfer-free effect is significant without, however, being total. The transfer-free properties can thus be adjusted as desired, which was impossible with the transfer-free compositions of the prior art, without harming the comfort of the film deposited.

The pigment(s)/polymer ratio by weight is preferably <1 and even ≦0.9. This ratio is preferably ≦0.5. This ratio can fall as far as 0.015. Above 0.5, the film transfers slightly and, above 1, the film transfers to a significant degree. These ranges includes all specific values and subranges therebetween, including 0.02, 0.05, 0.1, 0.2, 0.3, 0.4, 0.6, 0.7 and 0.8.

The composition of the invention can advantageously comprise at least 30% by weight of fatty phase with respect to the total weight of the composition. A granular and pulverulent texture is obtained below 30%. This is not very desirable when it is desired to obtain a non-granular homogeneous creamy appearance from a gel or a stick.

The pigments can be white or colored, inorganic and/or organic. Mention may be made, among inorganic pigments, of titanium dioxide, optionally treated at the surface, or zirconium or cerium oxides, as well as iron or chromium oxides, manganese violet, ultramarine blue, chromium hydrate and ferric blue. Mention may be made, among organic pigments, of carbon black, pigments of D & C type and lakes based on cochineal carmine or on barium, strontium, calcium or aluminum.

The pearlescent pigments can be chosen from white pearlescent pigments, such as mica covered with titanium oxide or with bismuth oxychloride, colored pearlescent pigments, such as titanium oxide-coated mica with iron oxides, titanium oxide-coated mica with in particular ferric blue or chromium oxide, or titanium oxide-coated mica with an organic pigment of the abovementioned type, as well as pearlescent pigments based on bismuth oxychloride.

The fillers can be inorganic or organic, lamellar or spherical. Mention may be made of talc, mica, silica, kaolin, nylon (Orgasol from Atochem), poly-β-alanine and polyethylene powders, Teflon, lauroyllysine, starch, boron nitride, polytetrafluoroethylene polymer powders, hollow microspheres, such as Expancel (Nobel Industrie), polytrap (Dow Corning) and silicone resin microbeads (Tospearls from Toshiba, for example), precipitated calcium carbonate, magnesium carbonate and carbonate hydroxide, hydroxyapatite, hollow silica microspheres (Silica Beads from Maprecos), glass or ceramic microcapsules, or metal soaps derived from organic carboxylic acids having from 8 to 22 carbon atoms, preferably from 12 to 18 carbon atoms, for example zinc, magnesium or lithium stearate, zinc laurate or magnesium myristate.

The fat-soluble colorants are, for example, Sudan red, DC Red 17, DC Green 6, β-carotene, soybean oil, Sudan brown, DC Yellow 11, DC Violet 2, DC Orange 5 or Quinoline yellow. They represent from 0.01 to 20% of the weight of the composition and better still from 0.1 to 6%. These ranges includes all specific values and subranges therebetween, including 0.02, 0.05, 0.2, 0.5, 1, 2, 3, 5, 10, 12 and 15% by weight.

The polymer of the composition of the invention makes possible the formation of a film on the skin, lips and/or mucous membranes which forms a network which traps the coloring materials and/or the active principles. Depending on the relative amount of coloring materials used, used with respect to the amount of stabilized polymer, it is possible to obtain a more or less glossy and more or less transfer-free film.

Mention may be made, as cosmetic, dermatological, hygiene or pharmaceutical active principles which can be used in the composition of the invention, of moisturizing agents, vitamins, essential fatty acids, sphingolipids or sunscreen agents. These active principles are used in an amount usual to a person skilled in the art and in particular at concentrations of 0.001 to 20% of the total weight of the composition.

The composition according to the invention can additionally comprise, according to the type of application envisaged, the constituents conventionally used in the fields under consideration, which are present in an amount appropriate to the desired pharmaceutical dosage form.

In particular, it can comprise, in addition to the liquid fatty phase in which the polymer is stabilized, additional fatty phases which can be chosen from waxes, oils, gums and/or pasty fatty substances of plant, animal, mineral or synthetic origin, indeed silicone origin, and their mixtures.

Mention may be made, among waxes which are solid at room temperature which can be present in the composition according to the invention, of hydrocarbon-comprising waxes, such as beeswax, carnauba wax, candelilla wax, ouricury wax, japan wax, cork fiber or sugarcane waxes, paraffin or lignite waxes, microcrystalline waxes, lanolin wax, montan wax, ozokerites, polyethylene waxes, waxes obtained by the Fischer-Tropsch synthesis, hydrogenated oils, fatty esters and glycerides which are solid at 25° C. It is also possible to use silicone waxes, among which may be mentioned alkyl, alkoxy and/or esters of polymethylsiloxane. The waxes can be provided in the form of stable dispersions of colloidal wax particles, such that they can be prepared according to known methods, such as those of "Microemulsions, Theory and Practice", edited by L. M. Prince, Academic Press (1977), pages 21–32, incorporated herein by reference. Mention may be made, as wax which is liquid at room temperature, of jojoba oil.

The waxes can be present in a proportion of 0–50% by weight of the composition and better still of 10 to 30%. These ranges includes all specific values and subranges therebetween, including 1, 2, 5, 8, 10, 12, 15, 18, 20, 25, 30, 35, 40 and 45% by weight.

The composition can additionally comprise any additive conventionally used in such compositions, such as thickeners, antioxidants, fragrances, preservatives or surfactants. Of course, a person skilled in the art will take care to choose this or these possible additional compounds and/or their amount so that the advantageous properties of the composition according to the invention are not, or not substantially, detrimentally affected by the envisaged addition.

In a specific embodiment of the invention, the compositions according to the invention can be prepared conventionally by a person skilled in the art. They can be provided in the form of a cast product and, for example, in the form of a stick or in the form of a dish which can be used by direct contact or with a sponge. In particular, they find an application as cast foundation, cast blusher or eyeshadow, lipstick, base or balm for caring for the lips, or products for concealing rings under the eyes. They can also be provided in the form of a supple paste, with a dynamic viscosity at 25° C. of the order of 1 to 40 Pa.s, or alternatively of a more or less fluid cream or gel. They can then constitute foundations or lipsticks, anti-sun products or products for coloring the skin.

The compositions of the invention are advantageously anhydrous and can comprise less than 5% of water with respect to the total weight of the composition. They can then be provided in particular in the form of an oily gel, of an oily liquid or oil, of a paste or of a stick or alternatively in the form of a vesicular dispersion comprising ionic and/or non-ionic lipids. These pharmaceutical dosage forms are prepared according to the methods usual in the fields under consideration.

These compositions for topical application can constitute in particular a cosmetic, dermatological, hygiene or pharmaceutical composition for protecting, treating or caring for the face, neck, hands or body (for example, anhydrous care cream, anti-sun oil or body gel), a make-up composition (for example, make-up gel) or an artificial tanning composition.

Having generally described this invention, a further understanding can be obtained by reference to certain specific examples which are provided herein for purposes of illustration only and are not intended to be limiting unless otherwise specified.

EXAMPLES

Example 1

Polymer Dispersion

A dispersion of non-crosslinked copolymer of methyl acrylate and of acrylic acid, in an 85/15 ratio, is prepared in isododecane, according to the method of Example 1 of EP-A-749,746, incorporated herein by reference, heptane being replaced by isododecane. A dispersion of particles of poly(methyl acrylate/acrylic acid) which are stabilized at the surface in isododecane by a polystyrene/copoly(ethylene-propylene) sequential diblock copolymer sold under the name of Kraton G1701 (Shell) is thus obtained which has a dry matter content of 22.6% by weight and a mean size of the particles of up to 175 nm (polydispersity: 0.05) and a Tg of 20° C. This copolymer can form a film.

Example 2

Lipstick

A lipstick is prepared in fluid form having the following composition:

| | |
|---|---|
| dispersion according to Example 1 | 90.7 g |
| parleam oil | 2.1 g |
| octyldodecanol | 0.9 g |
| PVP/eicosene | 1.2 g |
| phenyltrimethicone | 2.1 g |
| pigments | 3.0 g |

The pigments include a mixture of DC Red 27, DC Red 7, DC Red 36, of black iron oxide and of brown iron oxide.

The composition is prepared by simple mixing of the various constituents at room temperature, after milling the pigments in the oils. A lipstick is obtained which is easy to apply and which makes it possible to obtain a comfortable, supple and non-sticky film. This film is, in addition, glossy and completely "transfer-free". It withstands water perfectly well and is removed with a conventional make-up removal oil.

A sensory test was carried out with this lipstick on several people. The transfer-free test was carried out under the following conditions: application of the product to the lips, drying in the open air for 2 minutes and then application of the lips to a filter paper. This test is repeated under the same conditions with a drying time of 10 minutes. The freedom from transfer is judged as having an effectiveness of 98%.

Furthermore, the people in the transfer-free test considered the product easy to spread, conferring a homogeneous and adhesive make-up with a high degree of coverage and with a pronounced color. The contour of the lips is sharp. The texture of the product is considered fluid and pleasant on application. Removal of the make-up is carried out with a conventional make-up remover (Bifacil from Chez Lancôme) without leaving traces.

Example 3

Lipstick

A lipstick is prepared in the form of a stick having the following composition:

| | |
|---|---|
| dispersion of polymer (*) | 48.3 g |
| parleam oil | 7.0 g |
| octyldodecanol | 3.0 g |
| PVP/eicosene | 4.0 g |
| DC Red 27 | 2.2 g |
| phenyltrimethicone | 7.0 g |
| DC Red 7 | 4.2 g |
| DC Red 36 | 1.12 g |
| black iron oxide | 0.08 g |
| brown iron oxide | 2.4 g |
| polyethylene wax (Polywax 500) | 20.7 g |

The polymer is prepared according to the example with 95% of methyl acrylate and 5% of acrylic acid.

The composition is prepared as follows: milling of the pigments in the gently heated oils; addition of the polyethylene wax at 100° C.; slight cooling and then addition of the polymer dispersion and, finally, casting in an appropriate mold, in order to form a stick of lipstick.

A sensory test was carried out with this lipstick on several people in comparison with a lipstick of the state of the art (Colour Endure from L'Oréal). The transfer-free test was carried out under the following conditions: application of the product to the lips, drying in the open air for 2 minutes and then application of the lips to a filter paper. This test is repeated under the same conditions with a drying time of 10 minutes.

The application of the 2 products is equally easy. The act of applying make-up is more precise for the stick of the invention because the product is stiffer. The make-up is considered homogeneous for both products, more lively and more glossy with the stick of the invention. It is non-sticky for both products, with a light sensation, and does not give a taut feel. Transfer is more unobtrusive with the stick of the invention, it being known that the product of the prior art already had very good transfer-free properties. Removal of the make-up is easy for both products and does not leave a trace on the lips.

Example 4

Lipstick

A lipstick is prepared in fluid form having the following composition:

| | |
|---|---|
| dispersion according to Example 1 | 92.50 g |
| parleam oil | 1.35 g |
| PVP/hexadecene | 3.15 g |
| pigments | 3.0 g |

The pigments include a mixture of DC Red 27, DC Red 7, DC Red 36, of black iron oxide and of brown iron oxide.

This lipstick was prepared according to the implementation of Example 2. It is easily applied. The make-up is satiny, withstands water and exhibits very good transfer-free properties.

Gloss and Hardness Tests

A comparative composition C1 was prepared comprising 3% of pigments and the remainder to 100% of polymer dispersion according to Example 1. Furthermore, a composition according to the invention C2 was prepared comprising 3% of pigments, 4.5% of PVP/hexadecene and the remainder to 100% of polymer dispersion according to Example 1. A film of these compositions was deposited on contrast card and glass and then a hardness of 57 and 22 respectively and a gloss of 12.8 and 20.7 respectively were measured. The higher the hardness and gloss value, the harder and glossier the film. It is clearly found that the fat-soluble polymers clearly increase the gloss and the hardness of the film.

In order for a lipstick film to be right, the hardness must be less than 110 and better still less than 50. Furthermore, a glossy film is a film with a gloss greater than 60. A film with a gloss greater than 30 is satiny.

The hardness of the films was measured using a Persoz pendulum swinging on a film with a thickness of 300 µm obtained after drying for 24 h at 30° C. and 50% relative humidity (method according to Standard NF-T-30-016). The gloss is measured using a portable Byk Gardner glossmeter.

With a composition C3 according to the invention comprising 3% of pigments, 10% of PVP/hexadecene and the remainder with a polymer dispersion according to Example 1, a hardness of 29.2 and a gloss of 77.9 were obtained.

With a composition C4 according to the invention comprising 3% of pigments, 10% of PVP/hexadecene and the remainder to 100% of polymer dispersion according to Example 1, a hardness of 28.2 and a gloss of 83.5 were obtained.

With a composition C5 according to the invention comprising 10% of PVP/hexadecene and the remainder to 100% of polymer dispersion according to Example 1, a hardness of 35.8 and a gloss of 80.2 were obtained.

With a composition C6 according to the invention comprising 5% of PVP/hexadecene and the remainder to 100% of polymer dispersion according to Example 1, a hardness of 25.9 and a gloss of 66.6 were obtained.

Obviously, numerous modifications and variations of the present invention are possible in light of the above teachings. It is therefore to be understood that within the scope of the appended claims, the invention may be practiced otherwise than as specifically described herein.

This application is based on French Application Serial No. 97-16254, filed on Dec. 22, 1997, and incorporated herein by reference.

What is claimed is:

1. A composition suitable for topical application, comprising:
   a liquid fatty phase,
   at least one coloring agent,
   at least 2% by weight, with respect to the total weight of the composition, of a polymer which is dispersible in the liquid fatty phase, wherein the dispersible polymer is in the form of dispersed particles which are surface-stabilized by at least one stabilizing agent, and
   0.5% to 40% by weight of the total weight of the composition of a polymer which is soluble in the liquid fatty phase.

2. A composition, which is provided in the form of a cast product, and comprises:
   at least one cosmetic, dermatological, hygiene or pharmaceutical liquid fatty phase,
   at least one solid wax,
   at least 2% by weight, with respect to the total weight of the composition, of a polymer which is dispersible in the liquid fatty phase, wherein the dispersible polymer is in the form of dispersed particles which are surface-stabilized by at least one stabilizing agent, and
   0.5% to 40% by weight of the total weight of the composition of at least one polymer which is soluble in the liquid fatty phase.

3. A composition, comprising:
   a cosmetic, dermatological, hygiene or pharmaceutical volatile liquid fatty phase,
   at least 2% by weight, with respect to the total weight of the composition, of a polymer which can form a film and which is dispersible in the liquid fatty phase, wherein the dispersible polymer is in the form of dispersed particles which are surface-stabilized by at least one stabilizing agent,
   0.5% to 40% by weight of the total weight of the composition of at least one polymer which is soluble in the liquid fatty phase, and
   at least one active agent selected from the group consisting of cosmetic, dermatological, hygiene and pharmaceutical active agents.

4. The composition of claim 1, wherein the dispersible polymer can form a film.

5. The composition of claim 2, wherein the dispersible polymer can form a film.

6. The composition of claim 1, wherein the dispersible polymer can form a film.

7. The composition of claim 2, further comprising at least one coloring agent.

8. The composition of claim 3, further comprising at least one coloring agent.

9. The composition of claim 1, wherein the dispersible polymer is selected from the group consisting of radical polymers, polycondensates, polymers of natural origin and mixtures thereof.

10. The composition of claim 2, wherein the dispersible polymer is selected from the group consisting of radical polymers, polycondensates, polymers of natural origin and mixtures thereof.

11. The composition of claim 3, wherein the dispersible polymer is selected from the group consisting of radical polymers, polycondensates, polymers of natural origin and mixtures thereof.

12. The composition of claim 1, wherein the dispersible polymer is selected from the group consisting of polyurethanes, polyurethane-acrylics, polyureas, polyurea-polyurethanes, polyester-polyurethanes, polyether-polyurethanes, polyesters, polyesteramides, polyesters with a fatty chain or alkyds, acrylic and/or vinyl polymers or copolymers, acrylic-silicone copolymers, polyacrylamides, silicone polymers, fluorinated polymers, and mixtures thereof.

13. The composition of claim 2, wherein the dispersible polymer is selected from the group consisting of polyurethanes, polyurethane-acrylics, polyureas, polyurea-polyurethanes, polyester-polyurethanes, polyether-polyurethanes, polyesters, polyesteramides, polyesters with a fatty chain or alkyds, acrylic and/or vinyl polymers or copolymers, acrylic-silicone copolymers, polyacrylamides, silicone polymers, fluorinated polymers, and mixtures thereof.

14. The composition of claim 3, wherein the dispersible polymer is selected from the group consisting of polyurethanes, polyurethane-acrylics, polyureas, polyurea-polyurethanes, polyester-polyurethanes, polyether-polyurethanes, polyesters, polyesteramides, polyesters with a fatty chain or alkyds, acrylic and/or vinyl polymers or copolymers, acrylic-silicone copolymers, polyacrylamides, silicone polymers, fluorinated polymers, and mixtures thereof.

15. The composition of claim 1, wherein the liquid fatty phase comprises carbon-comprising, hydrocarbon-comprising, fluorinated and/or silicone oils of mineral, animal, plant or synthetic origin, alone or as a mixture.

16. The composition of claim 2, wherein the liquid fatty phase comprises carbon-comprising hydrocarbon-comprising, fluorinated and/or silicone oils of mineral, animal, plant or synthetic origin, alone or as a mixture.

17. The composition of claim 3, wherein the liquid fatty phase comprises carbon-comprising, hydrocarbon-comprising, fluorinated and/or silicone oils of mineral, animal, plant or synthetic origin, alone or as a mixture.

18. The composition of claim 1, wherein the liquid fatty phase is selected from the group consisting of:
   (a) liquid paraffin or liquid petrolatum, mink oil, turtle oil, soybean oil, perhydrosqualene, sweet almond oil, calophyllum oil, palm oil, parleam oil, grape seed oil, sesame oil, maize oil, rapeseed oil, sunflower oil, cottonseed oil, apricot oil, castor oil, avocado oil, jojoba oil, olive oil or cereal germ oil;
   (b) esters of lanolic acid, of oleic acid, of lauric acid or of stearic acid; and
   (c) fatty esters, higher fatty acids, higher fatty alcohols, silicone oils, which are optionally phenylated, or which are optionally substituted by aliphatic and/or aromatic groups or by functional groups, polysiloxanes modified by fatty acids, fatty alcohols or polyoxyalkylenes, fluorinated silicones or perfluorinated oils, or volatile oils.

19. The composition of claim 2, wherein the liquid fatty phase is selected from the group consisting of:
   (a) liquid paraffin or liquid petrolatum, mink oil, turtle oil, soybean oil, perhydrosqualene, sweet almond oil, calophyllum oil, palm oil, parleam oil, grape seed oil, sesame oil, maize oil, rapeseed oil, sunflower oil, cottonseed oil, apricot oil, castor oil, avocado oil, jojoba oil, olive oil or cereal germ oil;
   (b) esters of lanolic acid, of oleic acid, of lauric acid or of stearic acid; and
   (c) fatty esters, higher fatty acids, higher fatty alcohols, silicone oils, which are optionally phenylated, or which are optionally substituted by aliphatic and/or aromatic groups or by functional groups, polysiloxanes modified by fatty acids, fatty alcohols or polyoxyalkylenes, fluorinated silicones or perfluorinated oils, or volatile oils.

20. The composition of claim 3, wherein the liquid fatty phase is selected from the group consisting of:
   (a) liquid paraffin or liquid petrolatum, mink oil, turtle oil, soybean oil, perhydrosqualene, sweet almond oil, calophyllum oil, palm oil, parleam oil, grape seed oil, sesame oil, maize oil, rapeseed oil, sunflower oil, cottonseed oil, apricot oil, castor oil, avocado oil, jojoba oil, olive oil or cereal germ oil;
   (b) esters of lanolic acid, of oleic acid, of lauric acid or of stearic acid; and
   (c) fatty esters, higher fatty acids, higher fatty alcohols, silicone oils, which are optionally phenylated, or which are optionally substituted by aliphatic and/or aromatic groups or by functional groups, polysiloxanes modified by fatty acids, fatty alcohols or polyoxyalkylenes, fluorinated silicones or perfluorinated oils, or volatile oils.

21. The composition of claim 1, wherein the liquid fatty phase comprises:
   (a) non-aqueous liquid compounds having an overall solubility parameter according to the Hansen solubility space of less than 17 $(MPa)^{1/2}$,
   (b) monoalcohols having an overall solubility parameter according to the Hansen solubility space of less than or equal to 20 $(MPa)^{1/2}$, or
   (c) mixtures thereof.

22. The composition of claim 2, wherein the liquid fatty phase comprises:
   (a) non-aqueous liquid compounds having an overall solubility parameter according to the Hansen solubility space of less than 17 $(MPa)^{1/2}$,
   (b) monoalcohols having an overall solubility parameter according to the Hansen solubility space of less than or equal to 20 $(MPa)^{1/2}$, or
   (c) mixtures thereof.

23. The composition of claim 3, wherein the liquid fatty phase comprises:
   (a) non-aqueous liquid compounds having an overall solubility parameter according to the Hansen solubility space of less than 17 $(MPa)^{1/2}$,
   (b) monoalcohols having an overall solubility parameter according to the Hansen solubility space of less than or equal to 20 $(MPa)^{1/2}$, or
   (c) mixtures thereof.

24. The composition of claim 1, wherein the fatty phase comprises at least one oil which is volatile at room temperature.

25. The composition of claim 2, wherein the fatty phase comprises at least one oil which is volatile at room temperature.

26. The composition of claim 3, wherein the fatty phase comprises at least one oil which is volatile at room temperature.

27. The composition of claim 1, wherein the stabilizing agent is selected from the group consisting of sequential polymers, grafted polymers, random polymers and mixtures thereof.

28. The composition of claim 2, wherein the stabilizing agent is selected from the group consisting of sequential polymers, grafted polymers, random polyners and mixtures thereof.

29. The composition of claim 3, wherein the stabilizing agent is selected from the group consisting of sequential polymers, grated polymers, random polymers and mixtures thereof.

30. The composition of claim 27, wherein the stabilizing agent is selected from the group consisting of silicone polymers grafted with a hydrocarbon-comprising chain, hydrocarbon-comprising polymers grafted with a silicone chain, grafted copolymers having an insoluble backbone of polyacrylic with soluble grafts of polyhydroxystearic acid type, grafted or sequential block copolymers comprising at least one block of polyorganosiloxane and at least one block of a radical polymer, grafted or sequential block copolymers comprising at least one block of polyorganosiloxane type and at least one block of a polyether, copolymers of acrylates or methacrylates of $C_1$–$C_4$ alcohols and of acrylates or methacrylates of $C_8$–$C_{30}$ alcohols, grafted or sequential block copolymers comprising at least one block resulting from the polymerization of dienes and at least one block of a vinyl polymer, grafted or sequential block copolymers comprising at least one block resulting from the polymerization of dienes and at least one block of an acrylic polymer, and grafted or sequential block copolymers comprising at least one block resulting from the polymerization of dienes and at least one block of a polyether.

31. The composition of claim 28, wherein the stabilizing agent is selected from the group consisting of silicone polymers grafted with a hydrocarbon-comprising chain, hydrocarbon-comprising polymers grafted with a silicone chain, grafted copolymers having an insoluble backbone of polyacrylic with soluble grafts of polyhydroxystearic acid type, grafted or sequential block copolymers comprising at least one block of polyorganosiloxane and at least one block of a radical polymer, grafted or sequential block copolymers comprising at least one block of polyorganosiloxane type and at least one block of a polyether, copolymers of acrylates or methacrylates of $C_1$–$C_4$ alcohols and of acrylates or methacrylates of $C_8$–$C_{30}$ alcohols, grafted or sequential block copolymers comprising at least one block resulting from the polymerization of dienes and at least one block of a vinyl polymer, grafted or sequential block copolymers comprising at least one block resulting from the polymerization of dienes and at least one block of an acrylic polymer, and grafted or sequential block copolymers comprising at least one block resulting from the polymerization of dienes and at least one block of a polyether.

32. The composition of claim 29, wherein the stabilizing agent is selected from the group consisting of silicone polymers grafted with a hydrocarbon-comprising chain, hydrocarbon-comprising polymers grafted with a silicone chain, grafted copolymers having an insoluble backbone of polyacrylic type with soluble grafts of polyhydroxystearic acid type, grafted or sequential block copolymers comprising at least one block of polyorganosiloxane type and at least one block of a radical polymer, grafted or sequential block copolymers comprising at least one block of polyorganosiloxane type and at least one block of a polyether, copolymers of acrylates or methacrylates of $C_1$–$C_4$ alcohols and of acrylates or methacrylates of $C_8$–$C_{30}$ alcohols, grafted or sequential block copolymers comprising at least one block resulting from the polymerization of dienes and at least one block of a vinyl polymer, grafted or sequential block copolymers comprising at least one block resulting from the polymerization of dienes and at least one block of an acrylic polymer, and grafted or sequential block copolymers comprising at least one block resulting from the polymerization of dienes and at least one block of a polyether.

33. The composition of claim 30, wherein the stabilizing agent is a grafted or sequential block copolymer comprising at least one block resulting from the polymerization of a diene and at least one block of a vinyl polymer.

34. The composition of claim 31, wherein the stabilizing agent is a grafted or sequential block copolymer comprising at least one block resulting from the polymerization of a diene and at least one block of a vinyl polymer.

35. The composition of claim 32, wherein the stabilizing agent is a grafted or sequential block copolymer comprising at least one block resulting from the polymerization of a diene and at least one block of a vinyl polymer.

36. The composition of claim 1, wherein the soluble polymer is selected from the group consisting of alkylcelluloses with a saturated or unsaturated, linear or branched, $C_1$ to $C_8$ alkyl radical, silicone polymers which are compatible with the fatty phase and copolymers of vinylpyrrolidone, and mixtures thereof.

37. The composition of claim 2, wherein the soluble polymer is selected from the group consisting of alkylcelluloses with a saturated or unsaturated, linear or branched, $C_1$ to $C_8$ alkyl radical, silicone polymers which are compatible with the fatty phase and copolymers of vinylpyrrolidone, and mixtures thereof.

38. The composition of claim 3, wherein the soluble polymer is selected from the group consisting of alkylcelluloses with a saturated or unsaturated, linear or branched, $C_1$ to $C_8$ alkyl radical, silicone polymers which are compatible with the fatty phase and copolymers of vinylpyrrolidone, and mixtures thereof.

39. The composition of claim 1, wherein the polymer which is soluble in the liquid fatty phase is selected from the group consisting of copolymers of vinylpyrrolidone and of $C_8$ to $C_{22}$ alkene.

40. The composition of claim 2, wherein the polymer which is soluble in the liquid fatty phase is selected from the group consisting of copolymers of vinylpyrrolidone and of $C_8$ to $C_{22}$ alkene.

41. The composition of claim 3, wherein the polymer which is soluble in the liquid fatty phase is selected from the group consisting of copolymers of vinylpyrrolidone and of $C_8$ to $C_{22}$ alkene.

42. The composition of claim 39, wherein the polymer soluble in the liquid fatty phase is selected from the group consisting of copolymers of vinylpyrrolidone and of hexadecene.

43. The composition of claim 40, wherein the polymer soluble in the liquid fatty phase is selected from the group consisting of copolymers of vinylpyrrolidone and of hexadecene.

44. The composition of claim 41, wherein the polymer soluble in the liquid fatty phase is selected from the group consisting of vinylpyrrolidone and of hexadecene.

45. The composition of claim 1, further comprising at least one additional fatty phase chosen from waxes, gums and/or pasty fatty substances of plant, animal, mineral, synthetic or silicone origin, and their mixtures.

46. The composition of claim 2, further comprising at least one additional fatty phase chosen from waxes, gums and/or pasty fatty substances of plant, animal, mineral, synthetic or silicone origin, and their mixtures.

47. The composition of claim 3, further comprising at least one additional fatty phase chosen from waxes, gums and/or pasty fatty substances of plant, animal, mineral, synthetic or silicone origin, and their mixtures.

48. The composition of claim 1, wherein the coloring agent comprises at least one pulverulent compound selected from the group consisting of fillers, pigments and pearlescent agents.

49. The composition of claim 7, wherein the coloring agent comprises at least one pulverulent compound selected from the group consisting of fillers, pigments and pearlescent agents.

50. The composition of claim 8, wherein the coloring agent comprises at least one pulverulent compound selected from the group consisting of fillers, pigments and pearlescent agents.

51. The composition of claim 48, wherein the pulverulent compound and the polymer are present in a pigment(s)/polymer ratio of less than 1.

52. The composition of claim 49, wherein the pulverulent compound and the polymer are present in a pigment(s)/polymer ratio of less than 1.

53. The composition of claim 50, wherein the pulverulent compound and the polymer are present in a pigment(s)/polymer ratio of less than 1.

54. The composition of claim 48, wherein the pulverulent compounds comprise up to 40% of the total weight of the composition.

55. The composition of claim 49, the pulverulent compounds comprise up to 40% of the total weight of the composition.

56. The composition of claim 50, wherein the pulverulent compounds comprise up to 40% of the total weight of the composition.

57. The composition of claim 48, wherein the pulverulent compounds comprise from 1 to 30% of the total weight of the composition.

58. The composition of claim 49, wherein the pulverulent compounds comprise from 1 to 30% of the total weight of the composition.

59. The composition of claim 50, wherein the pulverulent compounds comprise from 1 to 30% of the total weight of the composition.

60. The composition of claim 1, wherein the dispersible polymer comprises, as dry matter, up to 60% of the total weight of the composition.

61. The composition of claim 2, wherein the dispersible polymer comprises, as dry matter, up to 60% of the total weight of the composition.

62. The composition of claim 3, wherein the dispersible polymer comprises, as dry matter, up to 60% of the total weight of the composition.

63. The composition of claim 1, wherein the dispersible polymer comprises, as dry matter, from 12 to 60% of the total weight of the composition.

64. The composition of claim 2, wherein the dispersible polymer comprises, as dry matter, from 12 to 60% of the total weight of the composition.

65. The composition of claim 3, wherein the dispersible polymer comprises, as dry matter, from 12 to 60% of the total weight of the composition.

66. The composition of claim 1, wherein the liquid fatty phase comprises at least one oil selected from the group consisting of $C_8$–$C_{16}$ isoparaffins, linear or cyclic silicones having from 2 to 7 silicon atoms, these silicones optionally comprising alkyl groups having from 1 to 10 carbon atoms, and mixtures thereof.

67. The composition of claim 2, wherein the liquid fatty phase comprises at least one oil selected from the group consisting of $C_8$–$C_{16}$ isoparaffins, linear or cyclic silicones having from 2 to 7 silicon atoms, these silicones optionally comprising alkyl groups having from 1 to 10 carbon atoms, and mixtures thereof.

68. The composition of claim 3, wherein the liquid fatty phase comprises at least one 20 oil selected from the group consisting of $C_8$–$C_{16}$ isoparaffins, linear or cyclic silicones having from 2 to 7 silicon atoms, these silicones optionally comprising alkyl groups having from 1 to 10 carbon atoms, and mixtures thereof.

69. The composition of claim 1, which is in the form of a stick; in the form of a supple paste, with a dynamic viscosity at 25° C. of the order of 1 to 40 Pa.s; in the form of a dish; of an oily gel; of an oily liquid; or of a vesicular dispersion comprising ionic and/or non-ionic lipids.

70. The composition of claim 2, which is in the form of a stick; in the form of a supple paste, with a dynamic viscosity at 25° C. of the order of 1 to 40 Pa.s; in the form of a dish; of an oily gel; of an oily liquid; or of a vesicular dispersion comprising ionic and/or non-ionic lipids.

71. The composition of claim 3, which is in the form of a stick; in the form of a supple paste, with a dynamic viscosity at 25° C. of the order of 1 to 40 Pa.s; in the form of a dish; of an oily gel; of an oily liquid; or of a vesicular dispersion comprising ionic and/or non-ionic lipids.

72. The composition of claim 1, which is in anhydrous form.

73. The composition of claim 2, which is in anhydrous form.

74. The composition of claim 3, which is in anhydrous form.

75. The composition of claim 1, which is in the form of a product for caring for and/or making up the skin and/or lips.

76. The composition of claim 2, which is provided in the form of a product for caring for and/or making up the skin and/or lips.

77. The composition of claim 3, which is provided in the form of a product for caring for and/or making up the skin and/or lips.

78. The composition of claim 1, which is provided in the form of a cast foundation, of a cast blusher or eyeshadow, of a lipstick, of a base or balm for caring for the lips, or of a product for concealing rings under the eyes.

79. The composition of claim 2, which is provided in the form of a cast foundation, of a cast blusher or eyeshadow, of a lipstick, of a base or balm for caring for the lips, or of a product for concealing rings under the eyes.

80. The composition of claim 3, which is provided in the form of a cast foundation, of a cast blusher or eyeshadow, of a lipstick, of a base or balm for caring for the lips, or of a product for concealing rings under the eyes.

81. The composition of claims 1, 2 or 3, wherein the polymer which is soluble in the liquid fatty phase is a copolymer of vinylpyrroidone.

82. A method of making the composition of claim 1, comprising combining
    the liquid fatty phase,
    the coloring agent,
    the polymer which is dispersible in the liquid fatty phase, and
    the polymer which is soluble in the liquid fatty phase.

83. A method of making the composition of claim 2, comprising combining
    the liquid fatty phase,
    the solid wax,
    the polymer which is dispersible in the liquid fatty phase, and
    the polymer which is soluble in the liquid fatty phase.

84. A method of making the composition of claim 3, comprising combining
    the liquid fatty phase,
    the polymer which can form a film and which is dispersible in the liquid fatty phase,
    the polymer which is soluble in the fatty phase, and
    the active agent.

85. A method of making the composition of claim 81, comprising combining the liquid fatty phase, the polymer which is dispersible in the liquid fatty phase, and the copolymer of vinylpyrrolidone which is soluble in the liquid fatty phase.

86. A method of treating skin or lips, comprising applying the composition of claim 1 to the skin or lips.

87. A method of treating skin or lips, comprising applying the composition of claim 2 to the skin or lips.

88. A method of treating skin or lips, comprising applying the composition of claim 3 to the skin or lips.

89. A method of treating skin or lips, comprising applying the composition of claim 81 to the skin or lips.

90. A method of limiting the transfer of the composition of claims 1, 2 or 3 onto a substrate other than the skin or the lips, comprising introducing, into the liquid fatty phase, at least one polymer which is dispersible in the liquid fatty phase, wherein the dispersible polymer is in the form of dispersed particles which are surface stabilized by at least one stabilizing agent and a viscosity increasing amount of at least one polymer which is soluble in the liquid fatty phase.

91. The composition of claim 1, wherein the gloss is greater than 30 as measured by a portable Byk Gardner glossmeter.

92. The composition of claim 2, wherein the gloss is greater than 30 as measured by a portable Byk Gardner glossmeter.

93. The composition of claim 3, wherein the gloss is greater than 30 as measured by a portable Byk Gardner glossmeter.

94. The composition of claim 81, wherein the gloss is greater than 60 as measured by a portable Byk Gardner glossmeter.

95. The composition of claim 1, wherein the gloss is greater than 60 as measured by a portable Byk Gardner glossmeter.

96. The composition of claim 2, wherein the gloss is greater than 60 as measured by a portable Byk Gardner glossmeter.

97. The composition of claim 3, wherein the gloss is greater than 60 as measured by a portable Byk Gardner glossmeter.

98. The composition of claim 81, wherein the gloss is greater than 60 as measured by a portable Byk Gardner glossmeter.

99. The composition of claim 1, wherein the hardness is less than 50 as measured by a Perosz pendulum swinging on a film with a thickness of 300 $\mu$m obtained after drying for 24 hours at 30° C. and 50% relative humidity.

100. The composition of claim 2, wherein wherein the hardness is less than 50 as measured by a Perosz pendulum swinging on a film with a thickness of 300 $\mu$m obtained after drying for 24 hours at 30° C. and 50% relative humidity.

101. The composition of claim 3, wherein wherein the hardness is less than 50 as measured by a Perosz pendulum swinging on a film with a thickness of 300 $\mu$m obtained after drying for 24 hours at 30° C. and 50% relative humidity.

102. The composition of claim 81, wherein wherein the hardness is less than 50 as measured by a Perosz pendulum swinging on a film with a thickness of 300 $\mu$m obtained after drying for 24 hours at 30° C. and 50% relative humidity.

103. The composition of claim 95, wherein the hardness is less than 50 as measured by a Perosz pendulum swinging on a film with a thickness of 300 $\mu$m obtained after drying for 24 hours at 30° C. and 50% relative humidity.

104. The composition of claim 96, wherein wherein the hardness is less than 50 as measured by a Perosz pendulum swinging on a film with a thickness of 300 $\mu$m obtained after drying for 24 hours at 30° C. and 50% relative humidity.

105. The composition of claim 97, wherein wherein the hardness is less than 50 as measured by a Perosz pendulum swinging on a film with a thickness of 300 $\mu$m obtained after drying for 24 hours at 30° C. and 50% relative humidity.

106. The composition of claim 98, wherein wherein the hardness is less than 50 as measured by a Perosz pendulum swinging on a film with a thickness of 300 $\mu$m obtained after drying for 24 hours at 30° C. and 50% relative humidity.

107. The composition of claim 1, wherein the at least one polymer which is soluble in the liquid fatty phase is present in an amount of 2% to 20% by weight of the total weight of the composition.

108. The composition of claim 2, wherein the at least one polymer which is soluble in the liquid fatty phase is present in an amount of 2% to 20% by weight of the total weight of the composition.

109. The composition of claim 3, wherein the at least one polymer which is soluble in the liquid fatty phase is present in an amount of 2% to 20% by weight of the total weight of the composition.

* * * * *

UNITED STATES PATENT AND TRADEMARK OFFICE
CERTIFICATE OF CORRECTION

PATENT NO. : 6,682,748 B1
DATED : January 27, 2004
INVENTOR(S) : Valerie De La Poterie et al.

It is certified that error appears in the above-identified patent and that said Letters Patent is hereby corrected as shown below:

<u>Column 16,</u>
Line 32, delete claim 6.

<u>Column 18,</u>
Line 53, "grated" should read -- grafted --;
Line 61, delete "type";
Line 64, "polyorganosiloxane type and" should read -- polyorganosiloxane and --.

<u>Column 19,</u>
Line 15, "acid type, grated" should read -- acid, grafted --;
Line 34, "polyacrylic type with" should read -- polyacrylic with --;
Line 35, "acid type, grafted" should read -- acid, grafted --;
Line 36, "type and at" should read -- and at --.

<u>Column 21,</u>
Line 4, "49, the" should read -- 49, wherein the --;
Line 50, "one 20 oil" should read -- one oil --.

<u>Column 22,</u>
Line 32, "vinylpyrroidone" should read -- vinylpyrrolidone --.

<u>Column 23,</u>
Line 6, "surface stabilized" should read -- surface-stabilized --;
Line 19, "60" should read -- 30 --;
Line 37, "2, wherein wherein the" should read -- 2, wherein the --.

UNITED STATES PATENT AND TRADEMARK OFFICE
CERTIFICATE OF CORRECTION

PATENT NO.    : 6,682,748 B1
DATED         : January 27, 2004
INVENTOR(S)   : Valerie De La Poterie et al.

It is certified that error appears in the above-identified patent and that said Letters Patent is hereby corrected as shown below:

<u>Column 24,</u>
Line 1, "3, wherein wherein the" should read -- 3, wherein the --.
Line 5, "81, wherein wherein the" should read -- 81, wherein the --.
Lines 14, 18 and 22, "wherein wherein" should read -- wherein --.

Signed and Sealed this

Twenty-ninth Day of June, 2004

JON W. DUDAS
*Acting Director of the United States Patent and Trademark Office*